(12) United States Patent
Mashak

(10) Patent No.: US 6,619,289 B1
(45) Date of Patent: Sep. 16, 2003

(54) CARBON DIOXIDE ABSORBER CANISTER WITH BREATHING GAS MOISTURE SUMP

(75) Inventor: James N. Mashak, Sun Prairie, WI (US)

(73) Assignee: Datex-Ohmeda, Inc., Madison, WI (US)

(*) Notice: Subject to any disclaimer, the term of this patent is extended or adjusted under 35 U.S.C. 154(b) by 21 days.

(21) Appl. No.: 09/780,262

(22) Filed: Feb. 9, 2001

(51) Int. Cl.[7] ................................................ C25D 5/34
(52) U.S. Cl. ............................. 128/205.28; 128/205.12
(58) Field of Search ...................... 128/203.28, 205.12, 128/205.21, 203.2; 422/122

(56) References Cited

U.S. PATENT DOCUMENTS

| | | | |
|---|---|---|---|
| 4,193,966 A | 3/1980 | Dowgul | 422/122 |
| 4,457,305 A | 7/1984 | Shanks et al. | 128/205.12 |
| 4,867,153 A | 9/1989 | Lorenzen et al. | 128/205.12 |
| 4,991,576 A | * 2/1991 | Henkin et al. | 128/203.28 |
| 5,168,868 A | 12/1992 | Hicks | 128/205.12 |
| 5,228,435 A | 7/1993 | Smith | 128/205.12 |
| 5,398,677 A | 3/1995 | Smith | 128/205.12 |
| 5,826,575 A | 10/1998 | Lall | 128/205.12 |

FOREIGN PATENT DOCUMENTS

WO 01/02034 1/2001

\* cited by examiner

Primary Examiner—Henry Bennett
Assistant Examiner—Sabrina Dagostino
(74) Attorney, Agent, or Firm—Andrus, Sceales, Starke & Sawall, LLP

(57) ABSTRACT

A moisture sump integrated into a carbon dioxide absorber canister provides a collection reservoir for condensate from a patient ventilator system when the carbon dioxide absorber canister is attached to the ventilator system. The volume of the moisture sump is appropriately sized so that the time interval required to collect a maximum amount of condensate interval is not more than the life expectancy of the carbon dioxide absorbing material contained within the canister. The moisture sump allows condensate management of difficult to drain areas such as the inlet to the expiratory check valve of a ventilator system. The removal of the carbon dioxide absorber canister by a patient attendee to replace the carbon dioxide absorbing material ensures that the condensate collected by the integral moisture sump is eliminated from the patient ventilator system.

17 Claims, 5 Drawing Sheets

CARBON DIOXIDE ABSORBER CANISTER WITH BREATHING GAS MOISTURE SUMP

FIELD OF THE INVENTION

This invention relates to patient ventilator systems in which breathing gas is circulated through a carbon dioxide absorber canister, and more particularly, to an improved carbon dioxide absorber canister having an integral moisture sump.

BACKGROUND OF THE INVENTION

In ventilator systems designed to provide respiratory gases to patients, condensation of water vapor commonly occurs in breathing circuit components due to the high humidity of patients' expired gases. Breathing circuits of the re-circulatory type include a carbon dioxide absorbing canister. Condensate is especially troublesome in carbon dioxide absorbing canisters and associated tubing and valves and may interfere with proper operation of the canisters and breathing circuit. When a patient requires prolonged use of a ventilator system, substantial condensate can accumulate, requiring medical personnel attending the patient to periodically rid the ventilator system of the excessive moisture.

Prior art ventilator systems have utilized various sumps to trap and remove condensate. The carbon dioxide absorbing canister itself has often been relied on as a common sump although the canister's primary function is removing carbon dioxide from the patient's expired breathing gases.

However, there exist areas in the breathing circuit that are difficult to drain to the carbon dioxide absorber canister. For example, the canister inlet structure, located upstream of the canister itself, including the expiratory check valve of the breathing system, is inherently difficult to maintain free of excessive condensate. In prior systems, the periodic actuation of a valve by a patient attendee was necessary for removal of condensate in this area.

Alternatively, separate stand-alone sumps have been employed specifically to drain the moisture from problematic areas. These sumps allowed the patient's attendees to view the collected moisture through a window or a transparent container so that the attendee could empty the collected moisture before the sump overflowed into the breathing circuit.

In practice, both the valve actuation mechanisms and the stand alone sump arrangements require extensive vigilance on the part of the patient's attendees. This demand on the attendees only adds to the already numerous ventilator servicing requirements which include removing and replacing spent carbon dioxide absorbing materials from the canister, ensuring proper composition of ventilator gases, maintaining desired gas volumes and pressures in the breathing circuit, and maintaining optimum humidity in inspiratory breathing gases. These varied tasks create multiple opportunities for operating errors to occur.

Therefore, an approach that avoids the above-described condensate-related problems and reduces condensate buildup problems in hard to drain breathing circuit areas, while simultaneously lowering the demands on the patient attendees, is highly desirable.

SUMMARY OF THE INVENTION

This invention is a carbon dioxide absorber canister with an integral moisture sump. The moisture sump collects condensate from areas of a breathing circuit that are difficult to drain to a common sump, such as the carbon dioxide absorber canister itself. The moisture sump found in the present invention may be integrally formed into the structure of the carbon dioxide absorber canister, the canister including a hollow container adapted to contain a carbon dioxide absorbing material.

The moisture sump includes a reservoir chamber for accepting collected condensate. The reservoir chamber may be arcuately-shaped with an upwardly facing entrance formed by surrounding walls. The entrance to the reservoir chamber offers a sealing surface for pneumatically sealing with the breathing circuit. This pneumatic seal is arranged so that the seal is accomplished by attachment of the carbon dioxide absorber canister to the patient ventilator system and is broken when the canister is subsequently removed from the system.

The moisture sump is adapted to collect condensate from breathing circuit areas proximate the inlet and outlet ports of the canister. Such areas include the inlet structures and outlet structures located in the patient ventilator system, specifically, the expiratory check valve and the inspiratory check valve. As noted above, the expiratory check valve is known to be a particularly troublesome area from which to drain condensed moisture.

The moisture sump's reservoir chamber may have a volume sized to accommodate the maximum amount of condensate collected in a given time interval, such as the life expectancy of the carbon dioxide absorbing material contained within the hollow container of the canister. Therefore, the patient's attendees are not required to monitor the moisture buildup in the moisture sump independently of other tasks. Removal of the carbon dioxide absorber canister from the breathing circuit automatically ensures that the condensed moisture contained in the integral sump is also removed.

Further advantages of a carbon dioxide absorber canister with an integral moisture sump of the present invention will be evident from the following detailed description and accompanying drawings.

DETAILED DESCRIPTION OF THE INVENTION

Like numerals are used to refer to like elements throughout the figures and the following description.

Figure 1:
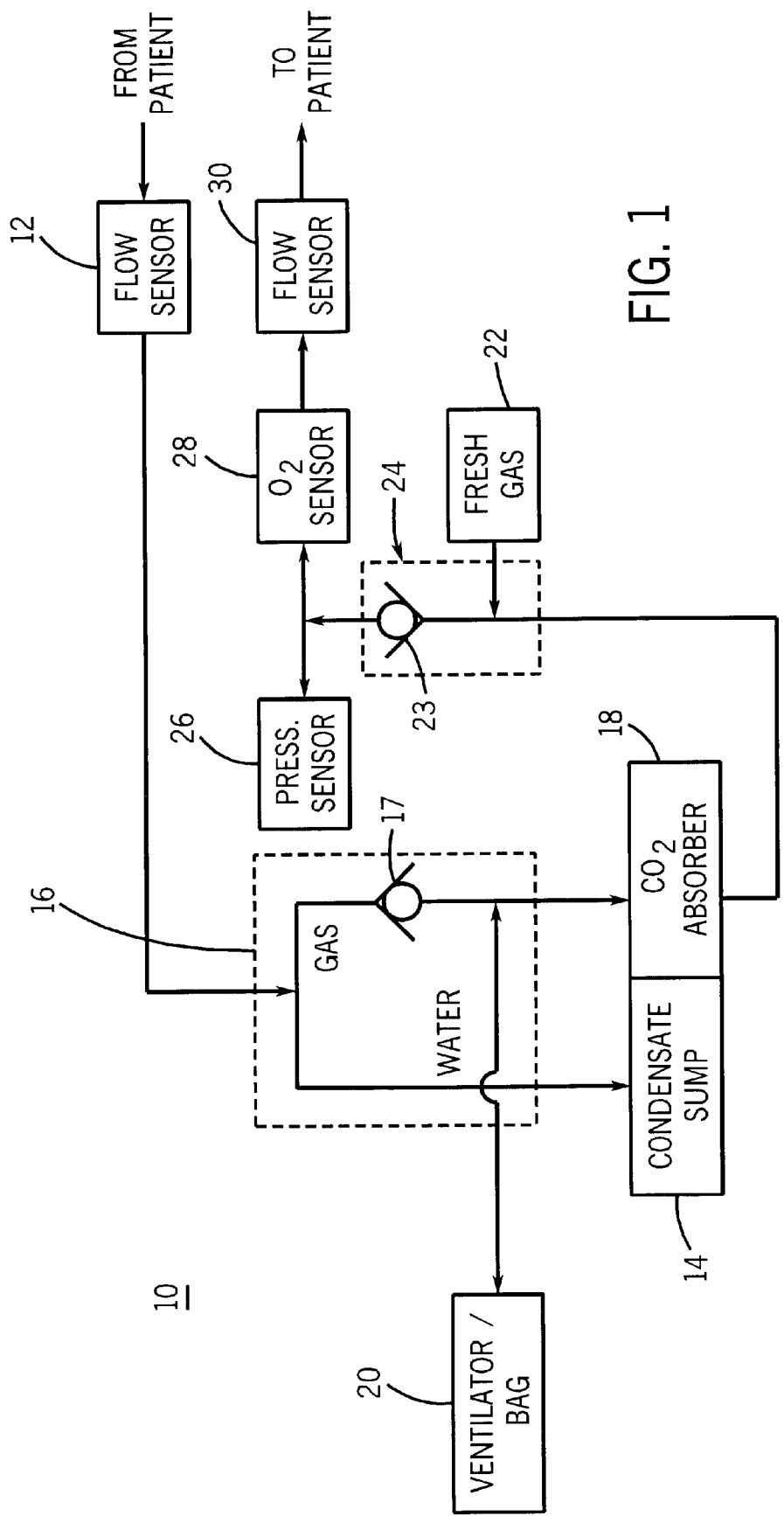
FIG. 1 is an overview of a ventilator breathing circuit showing elements of the circuit as distinct functional blocks.

FIG. 1 is an overview of a patient ventilator breathing circuit 10 showing elements of the circuit as distinct functional blocks. Exhaled breathing gases initially travel from the patient through a flow sensor 12. Flow sensor 12 provides output information to a patient attendee regarding flow characteristics of the exhaled gases. Expired breathing gases then flow to an expiration valve structure 16. In expiration valve structure 16, moisture is separated from the expired breathing gases and drains into moisture well or condensate sump 14. The breathing gases then pass through the expiratory check valve 17 contained in the structure 16 associated with a $CO_2$ absorber (canister) 18. Mechanical ventilator, or manually operated flexible bag, 20 is connected to the flow path for the breathing gases downstream of the expiratory check valve 17 to drive the re-circulating breathing gases through $CO_2$ absorber 18. Within $CO_2$ absorber 18, $CO_2$ gas is removed by contact with a $CO_2$ removing material, such as soda lime.

In FIG. 1, the functional blocks representing condensate well 14 and carbon dioxide absorber 18 are interconnected to graphically represent the integral design of these components found in the present invention. Also, and as shown in diagrammatic form in FIG. 1, moisture (water) carried by the breathing gases is removed from the gases before the gases pass through the expiratory check valve 17, thereby avoiding an excessive build up of moisture that could interfere with the operation of the valve 17. Further, removing moisture from the breathing gases upstream of the expiratory check valve 17 is advantageous in limiting or precluding moisture from entering ventilator/bag 20.

After the $CO_2$ content of the expiratory gas is reduced in canister 18, the expiratory gas exits $CO_2$ absorber 18 and fresh anesthesia gases, block 22, are added if necessary. The gases flow through an inspiratory check valve 23 located within an inspiratory valve structure 24 before being returned to the patient. Between the inspiratory check valve 24 and the patient, a pressure sensor 26, oxygen sensor 28, flow sensor 30, and other apparatus may be present.

Figure 2:
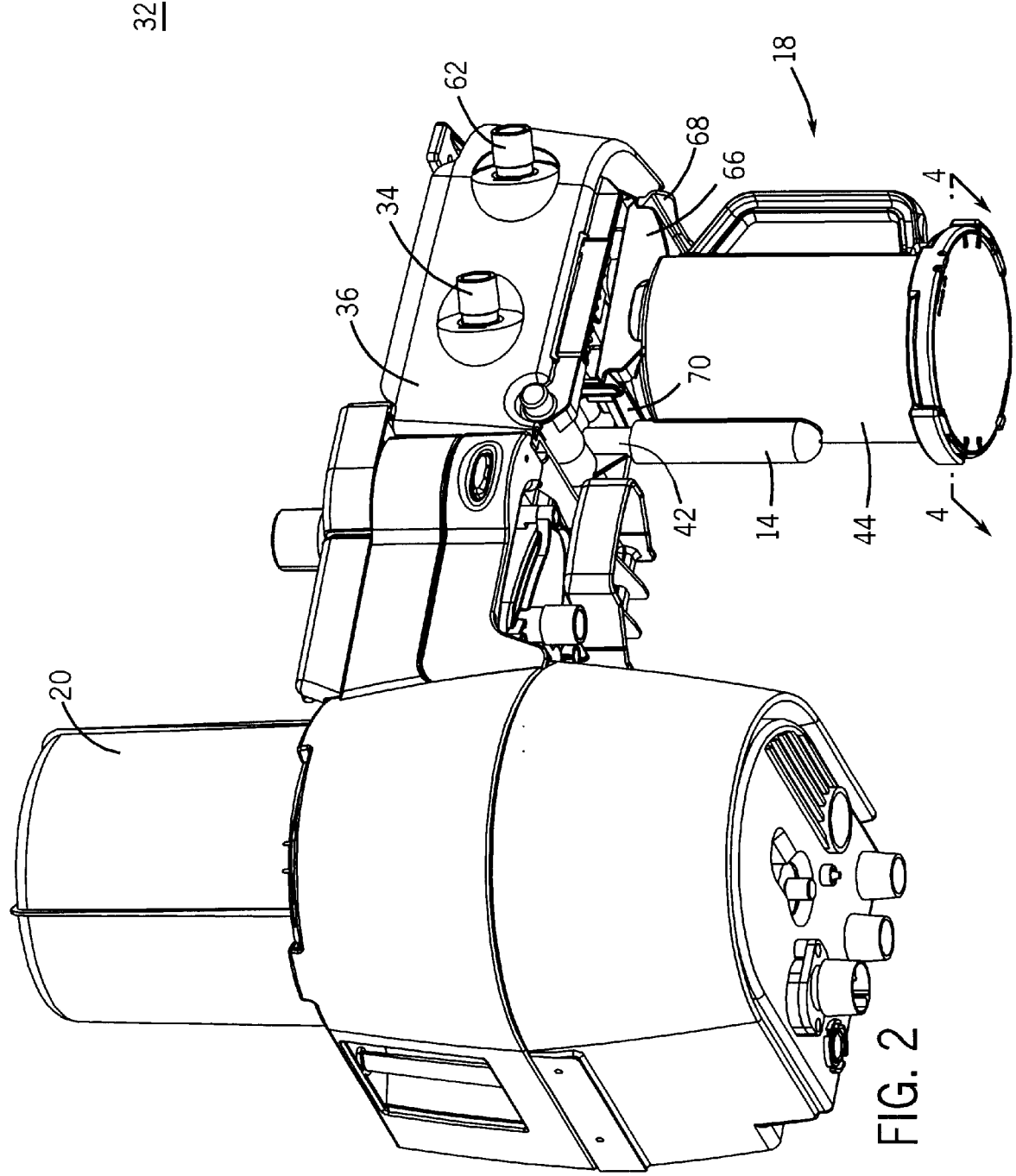
FIG. 2 is a perspective view of a patient ventilator system including one embodiment of the carbon dioxide absorber canister with moisture sump according to the invention.
Figure 3:
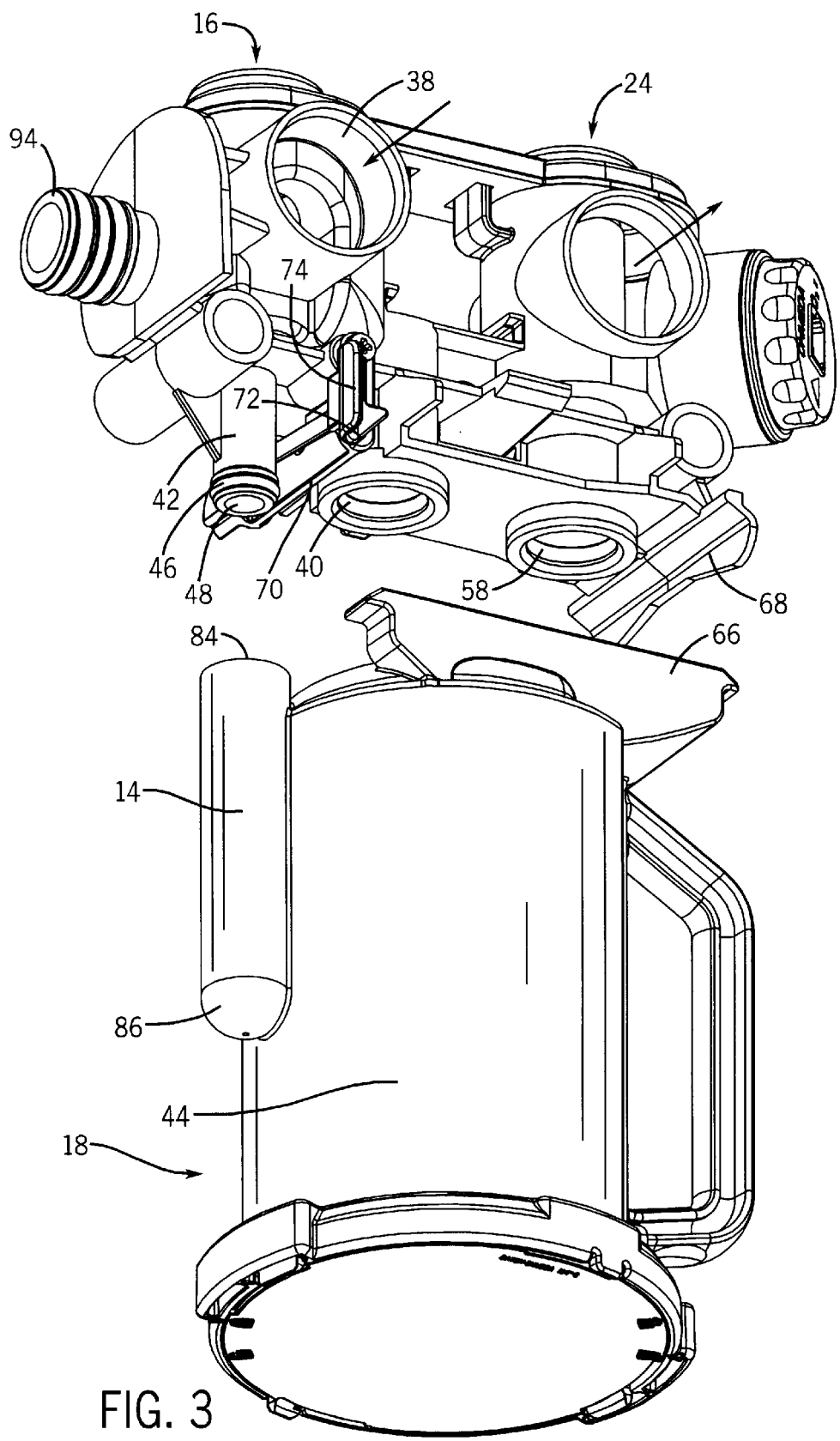
FIG. 3 is an exploded perspective view of the canister and associated valve structure depicted in FIG. 2.
Figure 4:
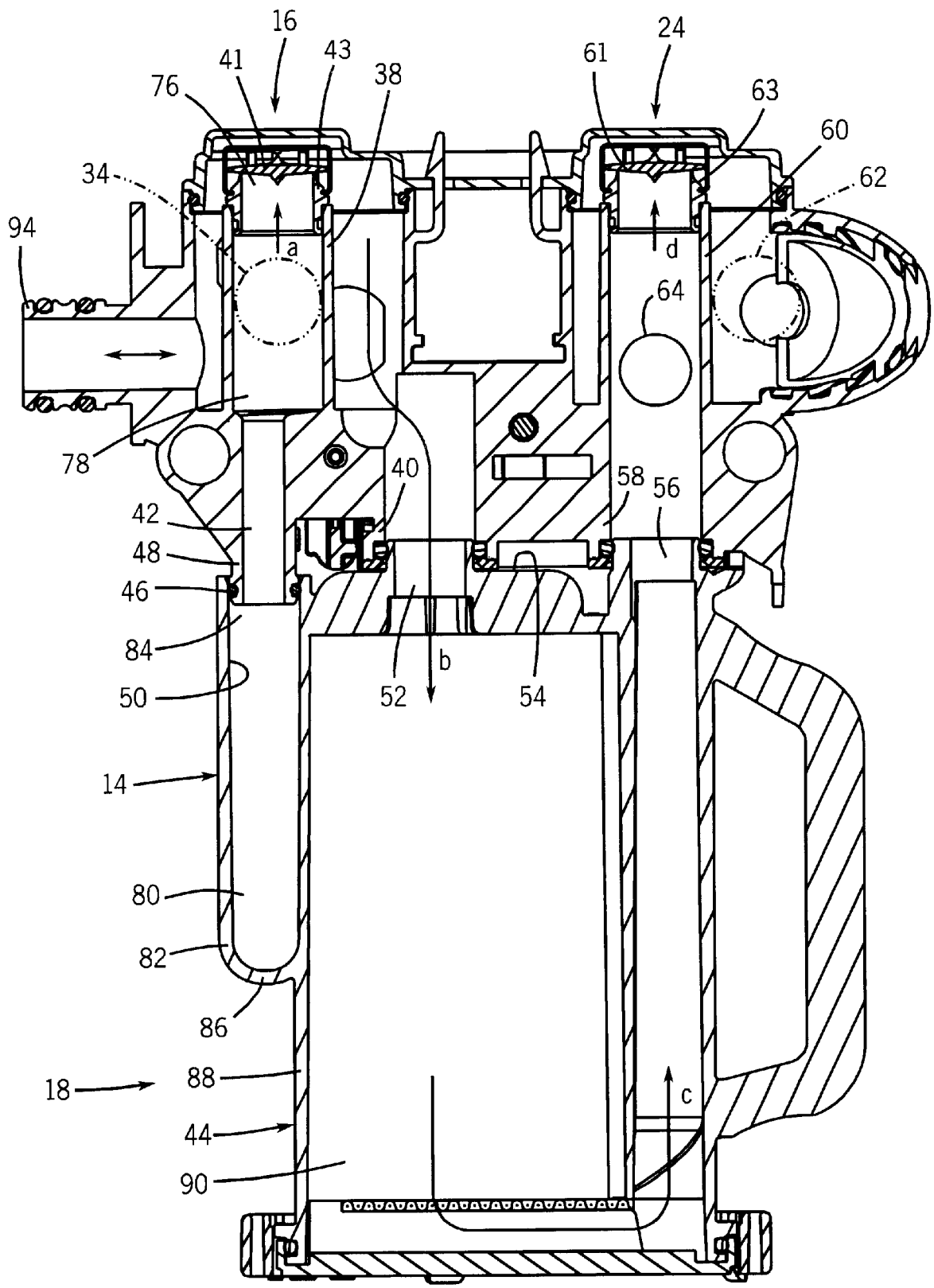
FIG. 4 is a cross-sectional view of the canister and associated valve structure shown in FIG. 2 taken generally along the line 4—4 of FIG. 2.

FIG. 2 depicts a patient ventilator apparatus 32 including a $CO_2$ absorber canister 18 with an integral moisture sump 14 according to the present invention. FIG. 3 shows an exploded perspective view of the apparatus of FIG. 2. FIG. 4 shows a cross-sectional view of the canister 18 with sump 14 of FIGS. 2 and 3.

Referring to FIGS. 2 and 3, a patient ventilator apparatus 32 includes a flow sensor module 36 partially enclosing a ventilator. 20, an expiratory valve structure 16 and an inspiratory valve structure 24. Expiratory valve structure 16 includes an expiratory valve inlet 34 seen protruding from ventilator housing 36 in FIG. 2. Expiratory valve inlet 34 communicates with the expiratory valve body 38 located within flow sensor module 36. Expiratory valve body 38 communicates with an expiratory valve outlet 40 located on the underside of the ventilator apparatus 32.

FIG. 4 illustrates that between inlet 34 and outlet 40, expiratory valve body 38 contains valve disk 41 mounted on valve seat 43 to control the passage of gas through the valve body 38. The expiratory valve structure 16 communicates with ventilator 20 through ventilator port 94. Ventilator port 94 is located downstream of the point in expiratory valve body 38, at which moisture is removed from the expiration gases. Condensed moisture reaching ventilator 20 is thus largely reduced.

As seen in FIGS. 2–4, expiratory valve body 38 includes an expiratory valve drain 42 adapted to collect and route condensed moisture away from the expiratory valve body 38. Condensate in the breathing circuit enters expiratory valve body 38 through valve inlet 34 and, unable to follow the upwardly leading path of the breathing gases shown by arrow a in FIG. 4, will drain to a lower portion 78 of the expiratory valve body 38. Condensate collected at the lower portion 78 then enters valve drain 42 and travels downward to reservoir chamber 80 of moisture sump 14. Reservoir chamber 80 is formed by sump wall 82 which extends from an upper entrance 84 downward to transition into a bottom 86. Lower portion 48 of drain tube 42 forms a pneumatic seal with reservoir chamber 80 through O-ring 46.

The preferred embodiment of the invention utilizes an arcuately-shaped reservoir chamber 80 formed by sump wall 82 which is integral with container wall 88 as shown in FIGS. 2–4. However, reservoir chamber 80 and container chamber 90 are physically isolated from each other, as shown in FIG. 4. Container body 44 and sump 14 are preferably molded as a single unit. Suitable materials may include polysulfones with polyphenyl sulfone being preferred since these materials can withstand autoclaving. Polypropylene would also be a suitable material for canister construction.

Expiratory valve outlet 40 forms a pneumatic seal with a canister inlet port 52 located on a top 54 of hollow container body 44. Expiratory gases exiting valve outlet 40 are conveyed in the direction of arrow b to container body 44 where they interact with a $CO_2$ absorbing material contained therein. The $CO_2$ absorbing material may be any material suitable for removing $CO_2$ from breathing gas. Soda lime is the preferred material.

As shown in FIG. 4, the breathing gases exit hollow container body 44 in the direction of arrow c through a canister outlet port 56 located on top 54 of container body 44. An inspiratory valve inlet 58 forms a pneumatic seal with the canister outlet port 56 and carries the breathing gases upward to the inspiratory valve body 60 (arrow d). Inspiratory valve body 60 is equipped with a gas flow controlling valve disk 61 and seat 63, and an inspiratory valve outlet 62 which is in communication with subsequent elements of the breathing circuit. A fresh breathing gas port 64 communicates with inspiratory valve body 60 so that fresh breathing gases may be introduced into the breathing circuit if so desired by patient attendees.

Canister 18 with integral sump 14 is secured to the expiratory valve outlet 40, expiratory valve moisture drain 42, and inspiratory valve inlet 58 through latches 66 located on top 54 of the hollow container body 44 which opposingly engage fixed latch receiving members 68 and movable-type latch receiving members 70. Movable type latch receiving members 70 are located on a latch actuator mechanism 72 which includes a latch actuator 74. The latch actuator 74 may be operated by a patient attendee to disengage the movable members 70 from the latches 66 to break the pneumatic seals between valves 16, 24, drain 42 and the carbon dioxide absorber canister 18 and moisture sump 14.

Following replacement of the $CO_2$ absorbing material and emptying of the moisture sump 14, the canister 18 with sump 14 may be reinstalled via the latching mechanism 72 to reestablish the pneumatic seals and consequently direct the expiratory gases of the breathing circuit past the moisture sump 14 and through container body 44.

As noted above, the container body 44 is adapted to contain an amount of $CO_2$ absorbing material, suitable for removing $CO_2$ from a given volume of breathing gases. The volume of the reservoir chamber 80 of sump 14 is appropriately sized to accommodate the maximum amount of condensate produced from the given volume. Therefore, a patient attendee need not be burdened with checking and removing/replacing a moisture sump separate from removing and replacing a $CO_2$ absorber canister.

The integrated moisture sump 14 acts as a trap for condensed moisture formed before expired gases reach canister 18. The invention ensures that not only the expiratory valve 16 remains free of condensed moisture but that excessive moisture does not build up in the container chamber 90 of the canister 18. This improvement allows for less erratic response of the expiratory valve 16 as well as increased life and efficiency of the $CO_2$ absorbing material.

Figure 5:
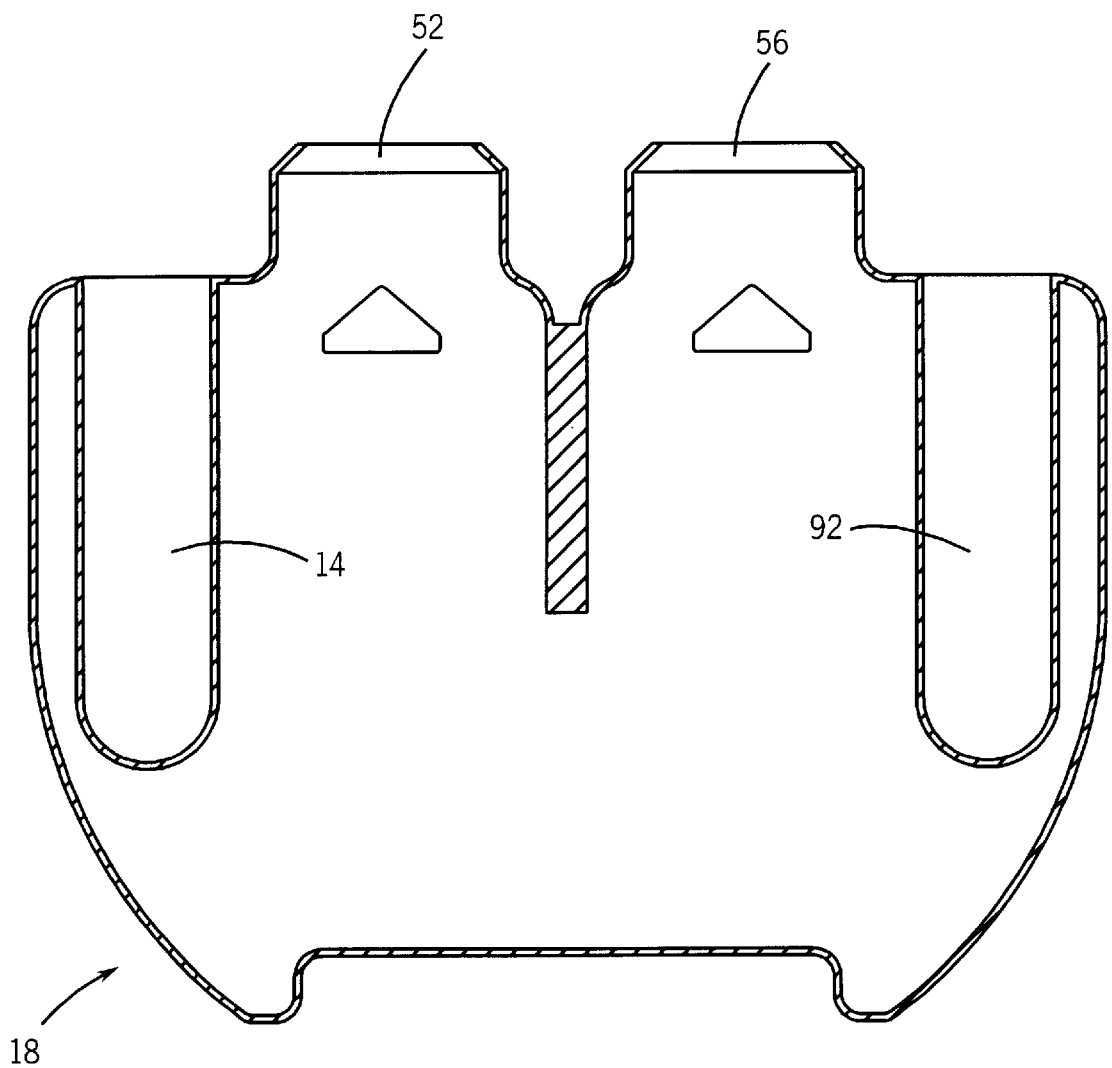
FIG. 5 is an alternate embodiment of the carbon dioxide absorber canister and moisture sump shown in a cross-sectional view similar to FIG. 4.

FIG. 5 depicts an alternative embodiment of the invention. FIGS. 1–4 show a single sump 14 on canister 18. In the embodiment shown in FIG. 5, a second moisture sump 92 provided on canister 18 to collect condensed moisture from an inspiratory valve drain (not shown) is alternately provided. The second moisture sump 92 shown in this embodiment resembles the first moisture sump 14 and appropriate modifications are made to canister 18 and valve structures 16 and 24.

Various alternatives and embodiments are contemplated as being within the scope of the following claims particularly pointing out and distinctly claiming the subject matter regarded as the invention.

I claim:

1. A canister for use with a patient breathing circuit in which expired breathing gases containing moisture are passed through the canister, said canister being removably insertable in the breathing circuit, said canister comprising:

a container through which the breathing gases pass when the canister is inserted in the breathing circuit, said container containing carbon dioxide absorbing material for removing carbon dioxide from the breathing gases; and a sump separate from said container but integrally formed in the canister with said container, said sump having an opening in fluid communication with the breathing gases for receiving and collecting moisture condensed out of the breathing gases passing through said container.

2. A canister according to claim 1 wherein the breathing gases flow along a flow path to the container and wherein said sump opens to the breathing gas flow path upstream of said container.

3. A canister according to claim 1 wherein the container has an external wall and the sump is integrally formed on the external wall.

4. A canister according to claim 1 wherein the container has an inlet port opening in a given direction and the sump has an entrance opening in the same given direction as the inlet port.

5. A canister according to claim 1 wherein the breathing circuit includes a valve structure and the canister is removably attached to the valve structure.

6. A canister according to claim 5 wherein the valve structure includes an expiratory valve.

7. A canister according to claim 6 wherein the canister is removably attached upstream of the expiratory valve along a flow path for the breathing gases.

8. A canister according to claim 5 wherein the canister is removably attached to the valve structure by a latching mechanism.

9. A canister according to claim 8 wherein the latching mechanism includes at least one latch provided on a top of the canister releasably engageable with at least one latch receiving member located proximate to the valve structure.

10. A canister according to claim 5 wherein the sump is removably attached to a drain in the valve structure.

11. A canister according to claim 10 wherein the sump and the drain are removably attached to form a pneumatic seal.

12. A canister according to claim 1 wherein the sump includes an arcuately-shaped reservoir chamber.

13. A canister according to claim 5 wherein the patient breathing circuit further comprises a further valve structure, the breathing gases entering the further valve structure after exiting the container, and wherein the canister includes a second sump integrally formed with the container and removably attached to said further valve structure for receiving and collecting moisture condensed out of the breathing gases.

14. A canister according to claim 13 wherein the second sump is removably attached to a drain in said second valve structure and has a second reservoir chamber adapted to store the collected condensate.

15. A canister according to claim 5 wherein:

the breathing circuit has a first valve structure with a first valve outlet, wherein the container has an inlet port, the inlet port of the first container forming, when the container is in an attached position, a pneumatic seal with the first valve outlet for directing breathing gases through the container; and wherein said breathing circuit has a second valve structure having an inlet, and wherein the container has an outlet port, said outlet port of the container, when the container is in an attached position, a pneumatic seal with the inlet of said second valve structure for discharging breathing gases from the container.

16. A canister according to claim 1 wherein the sump has a reservoir chamber having a volume sized so that a maximum amount of condensate collected in a given time interval is no more than the life expectancy of the carbon dioxide absorbing material contained within the container.

17. A canister for use with a patient breathing circuit in which expired breathing gases containing moisture are re-circulated, said breathing circuit having a valve for controlling the flow of gas in the breathing circuit, said canister being removably insertable in the breathing circuit so that the re-circulating breathing gases pass through the canister, said canister comprising:

a sump removably attached to the valve upstream of its flow controlling elements, the sump having a reservoir chamber adapted to store a collected condensate; and a container containing a carbon dioxide absorbing material, said re-circulating breathing gases passing through the container for removing $CO_2$ from the breathing gases;

the hollow container and sump being integrally formed so as to form a canister removably attached to the valve.

* * * * *